(12) United States Patent
Zardi et al.

(10) Patent No.: US 6,175,040 B1
(45) Date of Patent: Jan. 16, 2001

(54) REACTOR FOR TWO-PHASE REACTIONS, IN PARTICULAR FOR UREA SYNTHESIS AT HIGH PRESSURE AND TEMPERATURE

(75) Inventors: Federico Zardi, Breganzona (CH); Paolo Silva, Cemernate (IT)

(73) Assignee: Urea Casale SA, Lugano-Besso (CH)

( * ) Notice: Under 35 U.S.C. 154(b), the term of this patent shall be extended for 0 days.

(21) Appl. No.: 09/226,913

(22) Filed: Jan. 5, 1999

Related U.S. Application Data

(63) Continuation of application No. 08/491,998, filed on Jul. 18, 1995, now Pat. No. 5,888,460.

(30) Foreign Application Priority Data

May 11, 1994 (CH) .................................................. 1471/94
Dec. 23, 1994 (CH) .................................................. 3904/94

(51) Int. Cl.$^7$ ............................ C07C 273/04; B01J 8/04
(52) U.S. Cl. .......................... 564/67; 422/188; 422/189; 422/193
(58) Field of Search .............................. 564/67; 422/192, 422/189, 188

(56) References Cited

U.S. PATENT DOCUMENTS

| | | |
|---|---|---|
| 2,848,493 | 8/1958 | Dewling et al. . |
| 3,922,147 | 11/1975 | Sze et al. . |
| 4,051,206 | 9/1977 | Bunas et al. . |
| 4,341,640 | 7/1982 | Landis . |
| 4,356,132 | 10/1982 | Belyakov et al. . |
| 4,539,077 | 9/1985 | Jonckers et al. . |
| 5,223,238 | 6/1993 | Czuppon . |
| 5,304,353 | * 4/1994 | Dente et al. .......................... 422/193 |
| 5,573,735 | * 11/1996 | Pagani .................................. 422/189 |

FOREIGN PATENT DOCUMENTS

| | | |
|---|---|---|
| 1953994 | 5/1970 | (DE) . |
| 0487935 | 6/1993 | (EP) . |
| 1292316 | 10/1972 | (GB) . |
| 38813 | 8/1970 | (JP) . |

* cited by examiner

*Primary Examiner*—Shailendra Kumar
(74) *Attorney, Agent, or Firm*—Sughrue, Mion, Zinn, Macpeak & Seas, PLLC

(57) ABSTRACT

A reactor for two-phase reaction, in particular for urea synthesis at high pressure and temperature of the type wherein a co-current flow of a gaseous phase and a liquid phase takes place, comprises a substantially cylindrical vertical external shell (2) in which is supported a plurality of superimposed horizontal perforated plates (6a–6e) in mutually spaced relationship and at least one opening (12a–12e) for liquid flow being defined in correspondence of each of the perforated plates. Advantageously the openings (12a–12e) for liquid flow are mutually offset so as to obtain a substantially zigzag preferential flow path for the liquid phase in the reactor.

1 Claim, 3 Drawing Sheets

REACTOR FOR TWO-PHASE REACTIONS, IN PARTICULAR FOR UREA SYNTHESIS AT HIGH PRESSURE AND TEMPERATURE

This is a continuation of application Ser. No. 08/491,998 filed Jul. 18, 1995, now U.S. Pat. No. 5,888,460 the disclosure of which is incorporated herein by reference.

FIELD OF APPLICATION

In a general aspect, the present invention relates to a reactor for two-phase reactions, in particular for urea synthesis at high pressure and temperature of the type comprising:

- a substantially cylindrical vertical external shell,
- a plurality of superimposed perforated plates extending horizontally and in mutually spaced relationship in said shell, and
- at least one opening for liquid flow defined in correspondence of each of said perforated plates.

The present invention also relates to in-situ modernization of reactors for two-phase reactions, in particular for urea synthesis at high pressure and temperature.

In the description given below and in the following claims, the term: "in-situ" modernization, is understood to mean the on-site modification of a pre-existing reactor in order to improve its performance and obtain e.g. greater production capacity and/or greater conversion yield and/or reduction in energy consumption.

In the terminology of the field this type of modernization is also termed "retrofitting" or "revamping".

In the field of two-phase reactions at high pressure and temperature, e.g. for urea synthesis or hydrolysis, the requirement for increasing the conversion yield of synthesis reactors to improve their production capacity and reduce energy plant consumption in which said reactors operate is increasingly felt.

PRIOR ART

In order to satisfy said requirement synthesis reactors comprising a vertical tubular shell in which is supported a plurality of superimposed horizontal perforated plates in mutually spaced relationship have been becoming increasingly used.

The reaction product, e.g. urea, is obtained by placing in intimate contact a liquid phase and a gaseous phase comprising ammonia and carbon dioxide ($CO_2$) flowing in the shell from below upward.

The perforated plates have the function of mixing together said phases to facilitate their intimate contact and hence exchange of mass and heat indispensable for conversion of the reagents, ammonia and $CO_2$, into urea.

Synthesis reactors for two-phase reactions in accordance with the prior art are mainly of two types depending on the perforated plates used.

A first type of reactor as shown in FIG. 1 comprises a plurality of superimposed perforated plates extending horizontally over the entire cross section of the reactor and in which is defined a plurality of holes for the passing of a two-phase gas and liquid flow.

Since the liquid and gaseous phases pass through the same holes, there is alternating passing of gas and liquid with a pulsing flow which prevents intimate gas and liquid mixing. As a result there are low mass and heat transfer coefficients and hence low conversion yield.

In another case as shown in FIG. 3 the synthesis reactor comprises a plurality of superimposed horizontal perforated plates in mutually spaced relationship. Between the perimetric edge of each of these plates and the internal wall of the reactor is defined an annular aperture.

Even in this case however it is not possible to obtain the desired intimate mixing between the liquid phase and the gaseous phase because the liquid flows preferentially along said peripheral apertures while the gas tends to coalesce in the central part of the reactor.

Since they do not ensure effective intimate contact between the reagents the reactors in accordance with the prior art are not able to permit an optimal exchange of material and heat, which is the basic condition for achieving optimal conversion yield. Said reactors operate therefore far below their potential production capacity with resulting high energy consumption of the plant, e.g. for urea production, in which said reactors operate.

SUMMARY OF THE INVENTION

The technical problem underlying the present invention is to provide synthesis reactors capable of operating with high conversion yields so as to obtain greater production capacity and much lower energy consumption than those of the plants in accordance with the prior art mentioned above.

The above technical problem is solved in accordance with the present invention by a reactor of the above type, and characterized in that the openings for liquid flow defined in correspondence of at least two adjacent perforated plates are mutually offset.

In the description given below and in the following claims, the term: mutually offset openings, is understood to mean a plurality of openings essentially designed for the passing of the liquid phase, whose projection is not superimposed on the openings defined in correspondence of the adjacent perforated plates.

It has been found that thanks to the reactor in accordance with the present invention the liquid phase flows in the latter along an substantially zigzag preferential flow path which crosses the essentially vertical flow path of the gaseous phase.

In this manner it is possible to obtain continuous mixing of said phases along the entire flow path defined between adjacent perforated plates. There is thus advantageously increased the intimate contact between reagents with resulting increase of the mass and heat transfer coefficient between liquid and gas.

Advantageously the reactor in accordance with the present invention allows achievement of a high conversion yield optimizing the production capacity thereof and minimizing the energy consumption of the plant in which the reactor operates.

In a particularly advantageous and preferred embodiment of the present reactor at least one of the adjacent perforated plates is divided in a plurality of perforated sectors and unperforated sectors side by side.

Advantageously the perforated and unperforated sectors extend on said at least one perforated plate between an edge adjacent to the opening for liquid flow and an opposing edge adjacent to an internal wall of the shell.

Thanks to this particular configuration of the perforated plates it is possible to further increase the mixing between the gaseous phase and the liquid phase and hence the reactor yield.

Indeed the presence in the plates of the unperforated sectors facilitates penetration of the liquid phase flowing from one plate to the other along an essentially zigzag flow path into the gaseous phase which traverses the reactor along an essentially vertical flow path.

Practically, the liquid phase when it runs over a perforated plate is divided in a plurality of flows which cross the flows of the gaseous phase coming out from the perforated sectors of the plate. The gaseous flows in turn cause aspiration of the liquid flows running beside them.

This plurality of alternating liquid and gaseous flows in direct contact with each other has as a result an increase in the exchange surface between the phases during the passing of the latter from one plate to the next and thus causes an increase in the intimate contact between the reagents which facilitates transfer of material and heat.

The result obtained by the division of at least one perforated plate in perforated and unperforated sectors is thus faster and more intimate mixing of the liquid phase and the gaseous phase.

It was also found that optimal mixing is obtained when the perforated and unperforated sectors are substantially rectilinear, parallel and preferably when they have equal width.

Advantageously the openings for liquid flow in the reactor in accordance with the present invention are made up of diametrically opposed parts of the adjacent plates so as to maximize the liquid phase flow path between adjacent perforated plates to increase the intimate contact between the reagents.

In accordance with another aspect of the present invention there is also made available an in-situ modernization method for a reactor for two-phase reactions, in particular for urea synthesis at high pressure and temperature of the type wherein a co-current flow of a gaseous phase and a liquid phase takes place.

In a first embodiment the method of the present invention calls for in-situ modernization of a reactor for two-phase reactions, in particular for urea synthesis at high pressure and temperature of the type wherein a co-current flow of a gaseous phase and a liquid phase takes place, comprising a vertical tubular shell in which is supported a plurality of superimposed perforated plates in mutually spaced relationship, with said plates extending horizontally in said shell for the entire cross section thereof. In this case, the method is characterized in that it comprises the step of forming in at least two adjacent perforated plates respective mutually offset openings for liquid flow.

In a second embodiment the method in accordance with the present invention calls for in-situ modernization of a reactor for two-phase reactions, in particular for urea synthesis at high pressure and temperature of the type wherein a co-current flow of a gaseous phase and a liquid phase takes place, comprising a vertical tubular shell in which is supported a plurality of superimposed horizontal perforated plates in mutually spaced relationship, with at least one aperture defined between a perimetric edge of each of said plates and an internal wall of said shell. In this case the, method is characterized in that it comprises the step of partially obstructing the apertures defined in correspondence of at least two adjacent plates by means of baffles, with said baffles defining respective mutually offset openings for liquid flow.

In a third embodiment the method in accordance with the present invention calls for in-situ modernization of a reactor for two-phase reactions, in particular for urea synthesis at high pressure and temperature of the type wherein a co-current flow of a gaseous phase and a liquid phase takes place, comprising a vertical tubular shell in which is supported a plurality of superimposed horizontal perforated plates in mutually spaced relationship, with at least one aperture defined between a perimetric edge of each of said plates and an internal wall of said shell. In this case the, method is characterized in that it comprises the steps of obstructing the apertures defined in correspondence of at least two adjacent plates by means of baffles, and forming in said adjacent plates respective mutually offset openings for liquid flow.

In a preferred embodiment, the method of the present invention comprises additionally the step of providing in at least one of the adjacent perforated plates a plurality of perforated and unperforated sectors side by side.

Preferably the perforated and unperforated sectors side by side are provided by obstructing in preset zones the holes present in said at least one of said adjacent perforated plates.

As an alternative, the method of the present invention comprises additionally the step of providing in the shell at least one perforated plate comprising a plurality of perforated and unperforated sectors side by side.

The characteristics and advantages of the present invention are set forth in the description of an embodiment thereof given below by way of non-limiting example with reference to the annexed drawings.

Said description relates in particular to urea synthesis at high pressure and temperature. It is however clear that the following description can also be applied to other types of two-phase reactions such as for example urea hydrolysis reaction.

BRIEF DESCRIPTION OF THE DRAWINGS

In the drawings:

FIG. 5 also shows a longitudinal cross section view of a reactor obtained by modifying the reactor of FIG. 1 and FIG. 3 by the modernization method in accordance with another aspect of the present invention, FIG. 6 also shows a cross section view along C—C of FIG. 5 of a reactor obtained by modifying the reactor of FIG. 1, FIG. 8 also shows a cross section view along C—C of FIG. 5 of an alternative embodiment of the reactor obtained by modifying the reactor of FIG. 1.

DETAILED DESCRIPTION OF A PREFERRED EMBODIMENT

With reference to FIGS. 1–4, reference number 1 indicates as a whole a reactor particularly suitable for urea synthesis at high pressure (100–300 bar) and temperature (180–220° C.).

The reactor 1 comprises a vertical tubular shell 2 having at its ends nozzles 3, 4 respectively for inlet of cold and recycling reagents including ammonia and $CO_2$ and outlet of the reaction products. The reagents pass through the reactor 1 in the form of a liquid phase and a gaseous phase.

Figure 3:
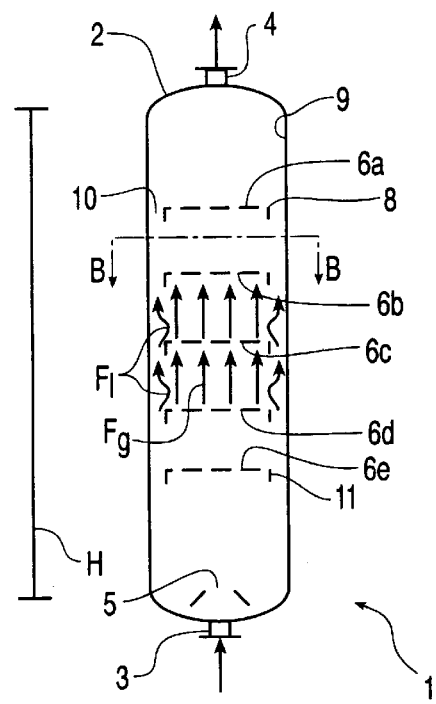
FIG. 3 shows a longitudinal cross section view of a conventional reactor for two-phase reactions in particular for urea synthesis at high pressure and temperature.
Figure 4:
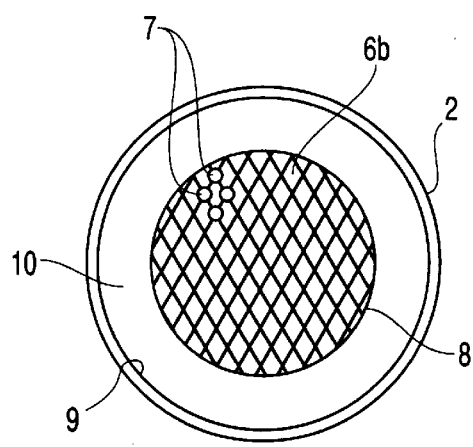
FIG. 4 shows a cross section view of the reactor of FIG. 3 along B—B of FIG. 3.

Reactors 1 of the type illustrated in FIG. 3, are usually provided with two independent outlet nozzles, not shown, for the separate outlet of a liquid phase and a gaseous phase respectively.

A deflector 5 is provided in the shell 2 near the nozzle 3 to deflect the flow of reagents entering the reactor 1.

6a–6e indicate a plurality of superimposed horizontal perforated plates in mutually spaced relationship. The plates 6a–6e have respective pluralities of holes all indicated by 7 and of predetermined size e.g. between 3 mm and 12 mm.

In general, the perforated plates are distributed along the useful height H of the reactor and have the function of distributing the gaseous phase in swarms of bubbles of small diameter to increase the material and heat exchange surface between the ammonia and the $CO_2$.

Figure 1:
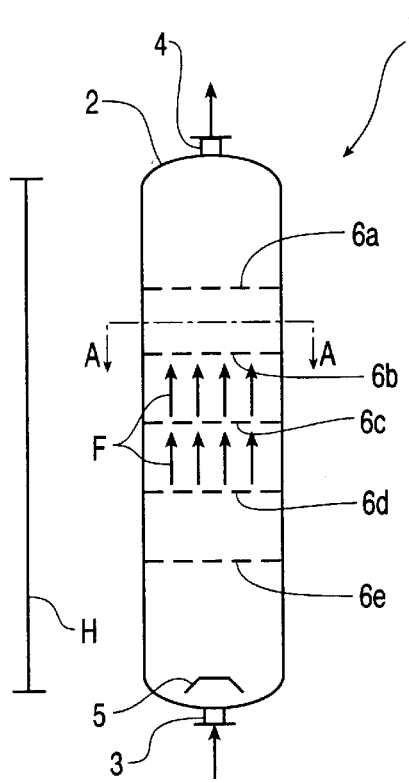
FIG. 1 shows a longitudinal cross section view of a conventional reactor for two-phase reaction, in particular for urea synthesis at high pressure and temperature.

In the example of FIG. 1 the perforated plates 6a–6e extend horizontally completely across the cross section of the shell 2.

In the example of FIG. 3 said perforated plates 6a–6e have a diameter smaller than the inside diameter of the shell 2, so as to define between a perimetric edge 8 of each plate 6a–6e and the internal wall 9 of the shell 2 an annular aperture 10.

The perforated plates 6a–6e of FIG. 3 are also provided with a collar 11 extending downward along the entire perimetric edge 8 of the plate.

In FIG. 1, the arrows F indicate the flow path of the reagents through the perforated plates 6a–6e. The behavior of the gaseous phase and the liquid phase in the reactor 1 is similar to that of a reactor with piston flow since liquid and gas cannot simultaneously pass through the holes 7 but are forced to do so alternately.

In FIG. 3, the arrows Fg and Fl indicate respectively flow paths of the gaseous phase and the liquid phase in the reactor 1.

Figure 5:
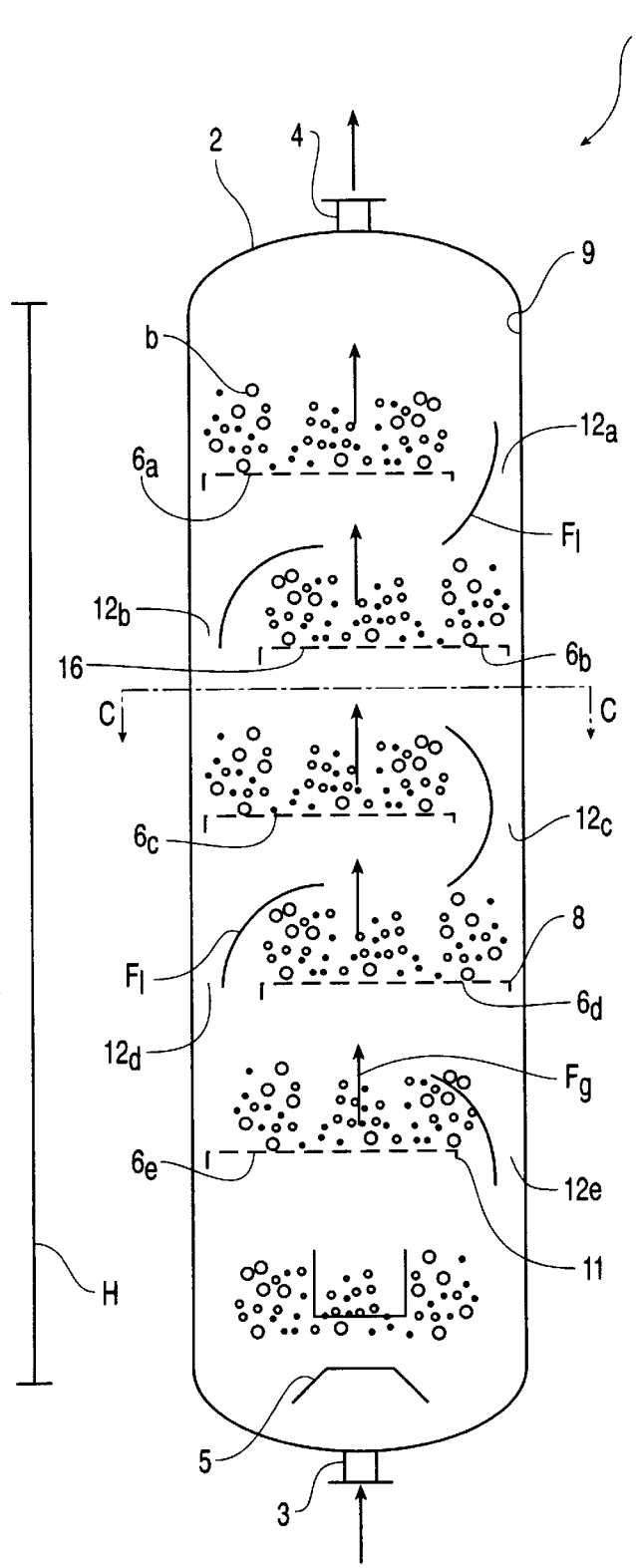
FIG. 5 shows a longitudinal cross section view of a reactor for two-phase reactions in particular for urea synthesis at high pressure and temperature in accordance with the present invention.

In FIG. 5, is indicated as a whole a reactor particularly suitable for urea synthesis at high pressure and temperature in accordance with the present invention.

In said figure the details of the reactor 1 structurally and functionally equivalent to those shown in FIGS. 1–4 are indicated by the same reference numbers and not further described.

In correspondence of at least two adjacent perforated plates 6a–6e of the reactor 1 of FIG. 5 are defined respective openings 12a–12e for liquid flow mutually offset so as to provide a preferential flow path for the liquid phase substantially in a zigzag pattern shown by the arrow Fl.

The perforated plates 6a–6e are supported in the shell in a conventional manner and are practically provided substantially adherent to the internal wall 9, except for a small gap of few millimeters to secure passivation against corrosion. Each opening 12a–12e for the liquid flow is in turn preferably defined by parts diametrically opposite in relation to the openings 12a–12e for liquid flow formed in the adjacent plates 6a–6e.

Figure 6:
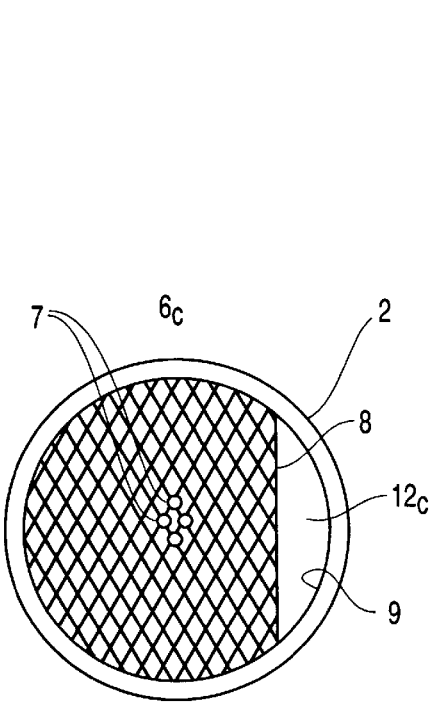
FIG. 6 shows a cross section view of the reactor in accordance with the present invention along C—C of FIG. 5.

In a preferred embodiment, the openings 12a–12e for liquid flow have a shape substantially of circular segment as shown in FIG. 6. Alternatively, the openings for liquid flow can be obtained by one or more substantially polygonal, circular or ellipsoidal shaped apertures.

The gaseous phase which is made to flow in the shell 2 in co-current along a vertical flow path as indicated in FIG. 5 by means of the arrow Fg is distributed by passing through the holes 7 in a swarm of small bubbles b which cross the liquid flow path defined between the adjacent perforated plates while mixing therewith.

In this manner it is possible to increase the intimate contact between the reagents and consequently obtain a high conversion yield while optimizing the production capacity of the reactor and minimizing energy consumption of the urea plant.

Particularly satisfying results were obtained with a cross section area of the openings 12a–12e for liquid flow between 1 and 10% of the surface of the cross section of the shell 2.

In accordance with an embodiment of the reactor in accordance with the present invention but not shown the openings 12a–12e for liquid flow in correspondence of the adjacent perforated plates 6a–6e can be defined alternately near the longitudinal axis of the shell and between a perimetric edge 8 of the plates and an internal wall 9 of the shell, respectively.

In the latter case there is obtained radial centrifugal/centripetal motion of the liquid phase.

FIG. 5 also shows a reactor particularly suitable for urea synthesis at high pressure and temperature obtained by modifying the reactor of FIG. 1 and FIG. 3 respectively, by a modernization method in accordance with a further aspect of the present invention.

In accordance with the first embodiment of the method in accordance with the present invention the reactor 1 of FIG. 1 is modernized by forming in at least two adjacent perforated plates 6a–6e respective openings 12a–12e for liquid flow mutually offset so as to provide a preferential flow path of the liquid phase substantially in a zigzag pattern shown in FIG. 5 by the arrow Fl.

With reference to FIG. 6 each of the openings (12a–12e) for liquid flow is preferably formed by means of removal of a peripheral portion of the plate between the internal wall 9 of the shell and the perimetric edge 8 of the plate.

In accordance with the second embodiment of the method in accordance with the present invention the reactor 1 of FIG. 3 is modernized by means of a step in which at least two adjacent annular apertures 10 are partially obstructed by baffles 13 defining respective openings 12a–12e for liquid flow mutually offset so as to provide a preferential zigzag flow path as described above.

This embodiment is particularly suitable with annular apertures 10 having a sufficient width so that the portion of the aperture 10 not obstructed by the baffle 13 will define an opening 12a–12e for liquid flow.

In this case, for sufficient width it is intended a width of the apertures 10 of at least 4 cm.

Figure 7:
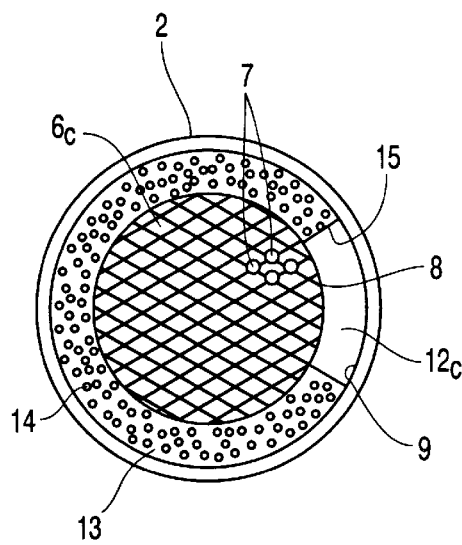
FIG. 7 shows a cross section view along C—C of FIG. 5 of a reactor obtained by modifying the reactor of FIG. 3.

As shown in FIG. 7 the baffles 13 preferably have a plurality of holes all indicated by 14, which increase the passing surface of the gaseous phase in correspondence of the adjacent plates 6a–6e.

The baffles 13 are removably supported in the shell 2 in a conventional manner known in itself between the perforated plates 6a–6e and the shell 2.

The openings 12a–12e for liquid flow realized by the above modernization method are preferably defined in diametrically opposite zones of the adjacent plates 6a–6e.

When the width of the apertures 10 is less than 4 cm, it is preferable to implement the third embodiment of the method in accordance with the present invention, which calls for in-situ modernization of the reactor of FIG. 3 by means of a first step wherein the annular apertures 10 defined in correspondence of at least two adjacent plates 6a–6e are obstructed by means of baffles 13, and a second step wherein in said adjacent plates 6a–6e respective mutually offset openings 12a–12e for liquid flow are formed, so as to provide a zigzag preferential flow path for the liquid phase in said shell.

Thanks to the modernization method in accordance with the present invention it is possible to obtain at low investment cost an increase in the conversion yield and production capacity of the modernized reactor while reducing energy consumption of urea plants.

Advantageously both the perimetric edge 8 of the plates 6a–6e of FIGS. 6 and 7 and the perimetric edge 15 of the baffles 13 of FIG. 7 are provided with a collar 11 of known type extending downward. The collar 11 forms together with the perforated plate 6a–6e and optionally with the baffle 13 a gas collecting chamber 16 so as to facilitate a continuous flow passage of the gaseous phase through the holes 7 and optionally 14.

It was also observed that the presence of the collar 11 facilitates the preferential zigzag flow path of the liquid phase between the openings 12a–12e for liquid flow.

Depending on the dimension of the synthesis reactor it will be quite easy for those skilled in the art to determine the optimal height of the collar 11. Generally the height of the collar 11 is between 100 mm and 300 mm.

Figure 8:
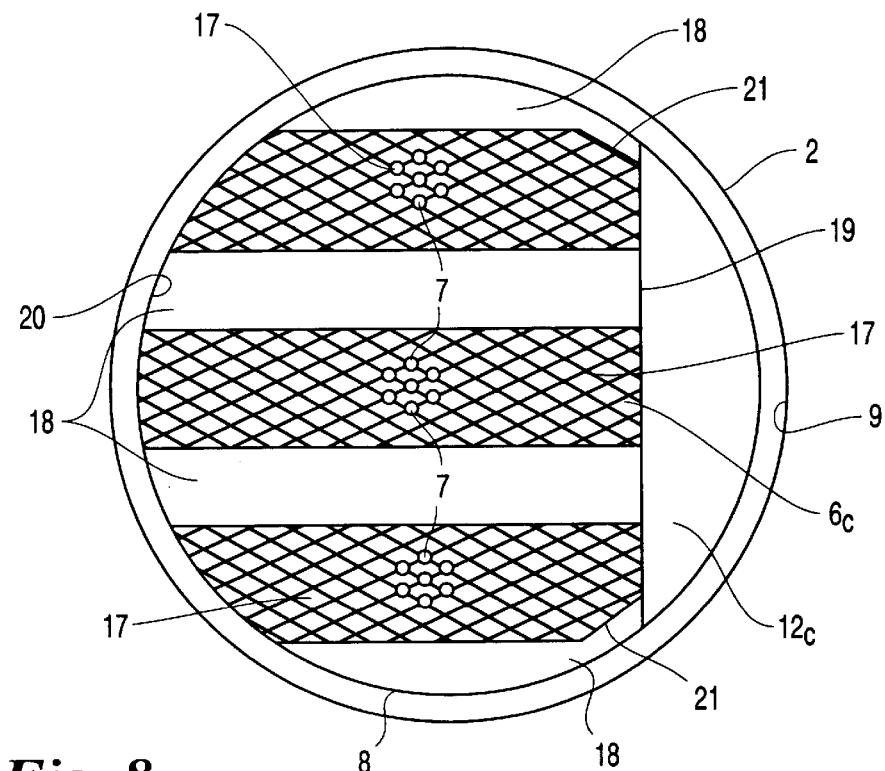
FIG. 8 shows a cross section view of an alternative embodiment of the reactor in accordance with the present invention along C—C of FIG. 5.

In a particularly advantageous and preferred embodiment of the reactor in accordance with the present invention in at least two adjacent perforated plates, e.g. plates 6b–6c, the lower perforated plate 6c is divided in perforated sectors 17 intercalated with unperforated sectors 18 as shown in FIG. 8.

The perforated sectors 17 and unperforated sectors 18 extend on the perforated plate 6c between an edge 19 adjacent to the opening 12c for liquid flow and an opposing edge 20 adjacent to the internal wall 9 of said shell 2.

In this manner the liquid phase and the gaseous phase flowing in the reactor are spontaneously divided in a plurality of alternating flows allowing a faster and more intimate phases mixing and hence an increase in synthesis reactor yield.

This flow alternation is made possible by the presence of unperforated sectors 18 along which runs the liquid phase, intercalated with perforated sectors 17 through which flows the gaseous phase.

To facilitate the passage of the liquid phase to the outermost sectors, the sectors adjoining said outermost sectors are tapered longitudinally near the edge 19 as indicated by the reference sign 21 in FIG. 8.

To obtain optimal mixing the perforated sectors 17 and unperforated sectors 18 are essentially rectilinear compatibly with the circular shape of the perforated plate 6c and are parallel and of equal width.

Figure 9:
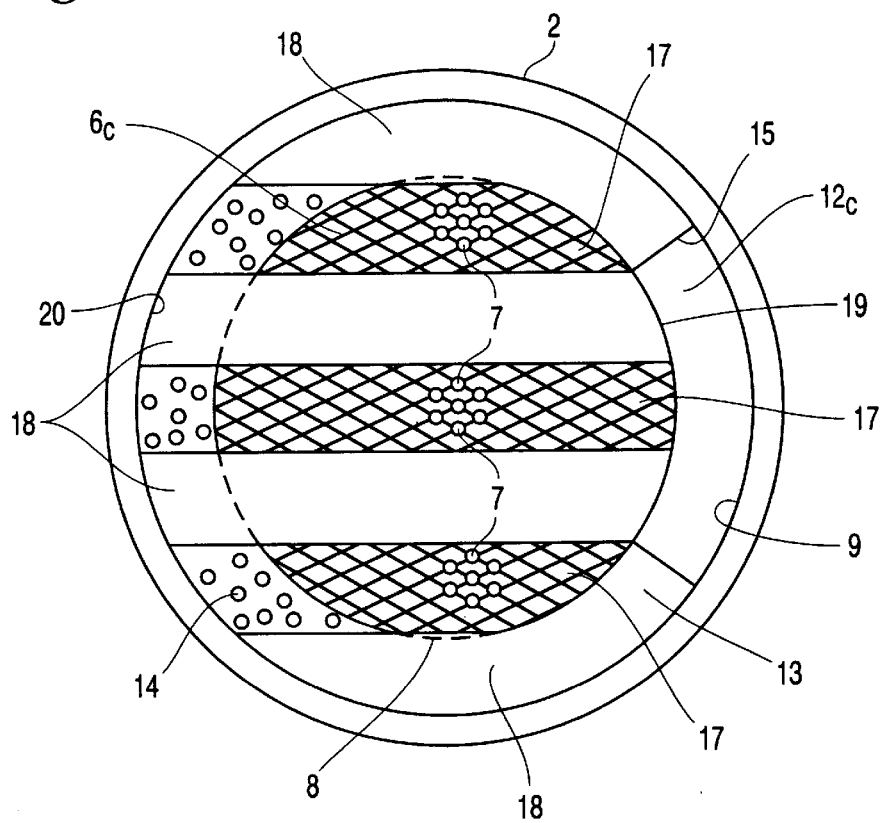
FIG. 9 shows a cross section view along C—C of FIG. 5 of an alternative embodiment of the reactor obtained by modifying the reactor of FIG. 3.

This division of the perforated plates 6a–6e in perforated sectors 17 and unperforated sectors 18 can be advantageously obtained even by the modernization method in accordance with the present invention which can include the step of providing in at least one of the adjacent perforated plates, e.g. the plate 6c, a plurality of perforated sectors 17 and unperforated sectors 18 side by side as shown in FIG. 8 and FIG. 9.

Preferably the perforated sectors 17 and unperforated sectors 18 side by side are provided by obstructing selectively the holes present in the plate 6c.

In an alternative form the modernization method in accordance with the present invention can include the step of providing in the shell 2 a perforated plate 6c including a plurality of perforated sectors 17 and unperforated sectors 18 side by side.

The perforated sectors 17 and unperforated sectors 18 thus obtained have the same structural and functional characteristics described above with reference to the embodiment of the reactor in accordance with the present invention.

Advantageously by means of urea synthesis reactor 1 of FIG. 5 it is also possible to implement a method for increasing the conversion yield and production capacity of a pre-existing reactor of the type wherein a co-current flow of a gaseous phase and a liquid phase takes place, the reactor comprising a vertical tubular shell in which are provided a plurality of superimposed horizontal perforated plates in mutually spaced relationship and in which is defined at least one opening for liquid flow in correspondence of each of said perforated plates, in the following manner.

In a first step the liquid phase is made to flow in the shell from below upward along an essentially zigzag liquid flow path defined between the openings.

In a second step the gaseous phase is made to flow in the shell from below upward along an essentially rectilinear gas flow path defined between the perforated plates and crossing the liquid flow path.

In a third step there is performed between the perforated plates a continuous mixing of the liquid phase with the gaseous phase flowing along the crossing liquid and gas flow paths.

In this manner it is possible to increase intimate contact and improve mass and heat transfer coefficients between liquid and gas.

The reactor for two-phase reactions in accordance with the present invention can be advantageously employed even for reactions such as urea hydrolysis at high pressure and temperature.

Indeed, the particular structural characteristics of the present invention make possible removal of urea contained in a liquid phase in aqueous solution by acting on the process parameters such as pressure, temperature, residence time and utilization of appropriate stripping agents.

This is performed by causing the liquid phase to flow in the reactor 1 of FIG. 5 from below upward along a substantially zigzag flow path defined between the openings 12a–12e for liquid flow and simultaneously subjecting to hydrolysis the urea contained in the liquid phase by means of a stripping agent in gaseous phase, e.g. steam under high pressure and temperature supplied from below upward along a substantially rectilinear flow path defined between the perforated plates 6a–6e, crossing the liquid path.

In this manner, between the perforated plates 6a–6e there takes place a continuous mixing of the liquid phase (solution including urea) with the gaseous phase (stripping agent) flowing along said crossing liquid and gas flow paths so as to increase their intimate contact and improve the mass and heat transfer coefficients to facilitate the urea hydrolysis reaction.

In the next example there are compared by way of merely indicative and non limiting example the conversion yields obtainable by a reactor in accordance with the present invention or modernized by the method of the present invention and by a reactor in accordance with the prior art.

EXAMPLE 1

Figure 2:
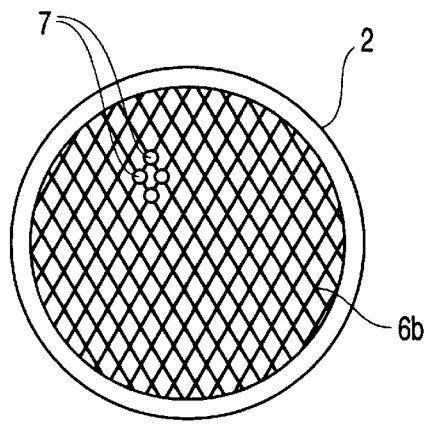
FIG. 2 shows a longitudinal cross section view of the reactor of FIG. 1 along A—A of FIG. 1.

In a urea production plant the conversion yield obtainable by a reactor in accordance with the present invention or modernized by the method of the present invention was compared with that obtainable by a conventional reactor as shown in FIGS. 1 and 2.

The two reactors considered have the following dimensions:

| | |
|---|---|
| Inside diameter of the shell: | 2.3 m |
| Useful height: | 35.0 m |

The operating conditions are the following:

| | | |
|---|---|---|
| Pressure: | | 155 ata |
| Temperature: | | 190° C. |
| Molar ratio, | $NH_3/CO_2$: | 3.3 |
| | $H_2O/CO_2$: | 0.6 |

The conventional reactor contains 10 perforated plates distributed along the useful height of the reactor and extending horizontally for the entire cross section of the shell.

In the reactor in accordance with the present invention, in correspondence of the perforated plates are defined openings for the liquid flow as shown in FIGS. 5 and 6 in circular segment shape, equal to 5% of the surface of the cross section of the shell. Along the perimetric edge of each of the perforated plates there was also provided a collar extending downward and having a height of 200 mm.

By means of a consolidated kinetic model described in the publication "Gas-Liquid Reactor in the Synthesis of Urea", M. Dente et al., Chemical Reactor Engineering, Vol. 47, n° Sep. 11, Jun. 8 1992, was then determined the conversion yield (in terms of molar %) of the $CO_2$ in urea coming out the reactor.

The conversion yield is set forth below:

| | |
|---|---|
| Conventional reactor: | 60.0% |
| Reactor according to the invention: | 63.0% |

An increase in yield of 3 percentage points in the reactor in accordance with the present invention is to be considered a very important result in the urea synthesis field because it permits reduction of the recycling of the unreacted products to the reactor of about 7–9% compared with the prior art, with a resulting considerable increase in the production capacity of the synthesis reactor and a reduction in energy consumption of the urea plant.

What is claimed is:

1. Method for increasing the conversion yield and production capacity of a reactor for urea synthesis at high pressure and temperature wherein a co-current flow of a gaseous phase and a liquid phase takes place in a vertical tubular shell (2) which is provided with a plurality of superimposed horizontal perforated plates (6a–6e) disposed in mutually spaced relationship with each plate having at least one opening (12a–12e) for liquid flow offset from an opening in an adjacent plate and a plurality of perforated sectors for gas flow separated from each other by unperforated sections, the method comprising the steps of:

causing said liquid phase to flow in said shell (2) from below upward along a substantially zigzag liquid flow path defined between said openings (12a–12e) for liquid flow, causing said gaseous phase to flow in said shell (2) from below upward along a gas flow path defined between said perforated plates (6a–6e) and crossing said liquid flow path, and performing between said perforated plates (6a–6e) continuous mixing of the liquid phase with the gaseous phase flowing along said crossed liquid and gas flow paths, wherein the liquid phase and the gaseous phase flowing upwardly from one perforated plate to the other are divided in a plurality of alternating liquid and gaseous flows, so as to increase intimate contact and improve mass and heat transfer.

\* \* \* \* \*